United States Patent
Kaplit

(10) Patent No.: US 7,477,997 B2
(45) Date of Patent: Jan. 13, 2009

(54) METHOD FOR ASCERTAINING INTERFERANTS IN SMALL LIQUID SAMPLES IN AN AUTOMATED CLINICAL ANALYZER

(75) Inventor: Michael Kaplit, Wilmington, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 45 days.

(21) Appl. No.: 11/311,532

(22) Filed: Dec. 19, 2005

(65) Prior Publication Data
US 2007/0143063 A1   Jun. 21, 2007

(51) Int. Cl.
G05B 19/048   (2006.01)
G05B 19/02    (2006.01)
G05B 19/04    (2006.01)
G05B 15/00    (2006.01)
G05B 15/02    (2006.01)
G05B 17/00    (2006.01)
G05B 17/02    (2006.01)
G06F 19/00    (2006.01)

(52) U.S. Cl. .............................. 702/55; 73/195; 73/198; 73/199; 73/861; 73/863; 73/863.01; 73/863.02; 73/864; 73/864.01; 73/864.11; 73/864.16; 221/9; 221/10; 222/1; 222/14; 222/52; 222/55; 222/64; 436/43; 436/54; 700/90; 700/231; 700/240; 702/1; 702/50; 702/189

(58) Field of Classification Search .............. 702/114, 702/1, 45, 50, 55, 127, 189; 73/34, 53.01, 73/195, 198, 199, 290 R, 861, 863, 863.01, 73/863.02, 864, 864.01, 864.11, 864.16; 221/9, 10; 222/1, 14, 21, 52, 55, 64; 436/43, 436/50, 54; 700/90, 231, 240
See application file for complete search history.

(56) References Cited

U.S. PATENT DOCUMENTS

| | | | | |
|---|---|---|---|---|
| 4,780,833 | A * | 10/1988 | Atake | 700/281 |
| 5,451,373 | A * | 9/1995 | Lewis et al. | 422/82.13 |
| 5,463,895 | A | 11/1995 | Brentz | 73/61.71 |
| 5,488,854 | A | 2/1996 | Kawanabe et al. | 73/19.05 |
| 5,488,874 | A | 2/1996 | Kawanabe et al. | 73/863.01 |
| 5,503,036 | A | 4/1996 | Nguyen et al. | 73/864.34 |
| 5,526,679 | A * | 6/1996 | Filippi et al. | 73/40.5 R |
| 5,537,880 | A | 7/1996 | Takeda et al. | 73/864.25 |
| 5,540,081 | A | 7/1996 | Takeda et al. | 73/37 |
| 5,547,875 | A * | 8/1996 | Petty et al. | 436/8 |
| 5,554,811 | A | 9/1996 | Rokugawa et al. | 73/864.34 |
| 5,622,869 | A | 4/1997 | Lewis et al. | 436/148 |
| 5,637,799 | A | 6/1997 | Heyman et al. | |
| 5,723,795 | A | 3/1998 | Merriam | 73/863 |
| 5,750,881 | A | 5/1998 | Dorenkott et al. | 73/37 |
| 5,814,275 | A * | 9/1998 | Lewis et al. | 422/63 |
| 5,883,301 | A * | 3/1999 | Filippi et al. | 73/40.5 R |
| 5,915,282 | A | 6/1999 | Merriam et al. | 73/863 |
| 5,965,828 | A | 10/1999 | Merriam | 73/863 |
| 6,022,747 | A | 2/2000 | Gherson et al. | 436/69 |
| 6,060,320 | A | 5/2000 | Dorenkott et al. | 436/54 |
| 6,121,049 | A | 9/2000 | Dorenkott et al. | 436/50 |
| 6,158,269 | A | 12/2000 | Dorenkott et al. | 73/37 |
| 6,250,130 | B1 * | 6/2001 | Howard et al. | 73/1.36 |
| 6,370,942 | B1 * | 4/2002 | Dunfee et al. | 73/37 |
| 7,150,190 | B2 * | 12/2006 | Krufka et al. | 73/304 C |

(Continued)

Primary Examiner—Edward R Cosimano
(74) Attorney, Agent, or Firm—Leland K. Jordan

(57) ABSTRACT

A liquid aspiration method which includes a method for determining the quality of the aspirated sample through mathematical analysis of the standard deviation of the residuals of the linear regression analysis of the aspiration pressure profile generated between the onset of actual aspiration and the end of actual aspiration and comparison of the results with predetermined known values.

3 Claims, 6 Drawing Sheets

U.S. PATENT DOCUMENTS

| | | |
|---|---|---|
| 2003/0092185 A1* | 5/2003 | Qureshi et al. ................. 436/43 |
| 2006/0207322 A1* | 9/2006 | Krufka et al. ............. 73/304 C |
| 2007/0062250 A1* | 3/2007 | Krulevitch et al. ........... 73/1.16 |
| 2007/0062251 A1* | 3/2007 | Anex .......................... 73/1.36 |
| 2007/0093753 A1* | 4/2007 | Krulevitch et al. .......... 604/131 |
| 2007/0128047 A1* | 6/2007 | Gonnella et al. ................ 417/2 |
| 2007/0143063 A1* | 6/2007 | Kaplit ........................ 702/140 |
| 2008/0010030 A1* | 1/2008 | Cheung et al. ................. 702/34 |
| 2008/0109185 A1* | 5/2008 | Cheung et al. .............. 702/184 |

* cited by examiner

METHOD FOR ASCERTAINING INTERFERANTS IN SMALL LIQUID SAMPLES IN AN AUTOMATED CLINICAL ANALYZER

FIELD OF THE INVENTION

The present invention relates to the transfer of an amount of liquid from one container to another, and more particularly, to an improved method for ascertaining, the integrity of a liquid aspiration process using a vacuum actuated pipette.

BACKGROUND OF THE INVENTION

Fully automated diagnostic analyzers are commercially available to perform chemical assays and immunoassays of biological fluids such as urine, blood serum, plasma, cerebrospinal liquids and the like. Generally, reactions between an analyte in a patient sample and reagents used during the assay result in generating some sort of signal that can be measured by the analyzer. From this signal the concentration of analyte in the patient sample may be calculated. Such automated analyzers generally use an aspirating means such as a sampling tip, or probe or needle, to transfer desired volumes of liquid samples or liquid reagents between receptacles, such as between sample containers, reagent containers and reaction cuvettes disposed on the analyzer. Hereinafter, variations of the term aspirate refer to all of such processes for extracting liquid from one container and depositing at least some of the liquid into the same or another container and further includes the supporting devices required to complete the liquid handling operations.

Aspirators typically comprise an elongated, needle-like probe or pipette having a hollow passage whereby liquid may be aspirated into and/or dispensed from the probe using appropriate pumping resources. The pipette may be carried by a transport mechanism adapted to provide horizontal and vertical movement so as to enable the pipette tip to be lowered into a liquid in a reservoir for aspiration of the liquid, and for transporting the liquid to a another location whereat the pipette is lowered to an optimal position for dispensing the liquid. Some type of device, such as a piston assembly, which may be incorporated into the pipette, is operated electronically to aspirate liquid into the pipette and to dispense liquid from the pipette using vacuum pressures.

It is desirable, when aspirating a liquid, to accurately determine if any abnormalities or non-uniformities within the liquid have adversely affected the overall quality of the aspiration process. Non-uniformities such as clots, bubbles, foam, insufficient volume, etc, may exist in liquids, particularly when the liquid is one of several body fluids being analyzed as these frequently are of a non-uniform composition. Various methods have been developed to detect the effect of such non-uniformities on the aspiration process.

U.S. Pat. No. 6,370,942 discloses an method for evaluating the quality of a liquid aspiration for undesirable events such as partial or complete clogs, or aspiration of air by employing three separate aspiration tests including a pressure difference test to verify liquid was aspirated, a pressure recovery test to check for clogs and aspiration of unwanted cells, and a pressure shape test to check for abnormalities during aspiration, such as clogs, air aspiration, density changes (due to aspiration of blood cells), etc. Three algorithms are employed, and each must produce a positive result for the sample to be released for transfer elsewhere.

U.S. Pat. No. 6,022,747 discloses a blood clot detector having a pressure transducer on an aspiration line to provide output voltage data to a microprocessor corresponding to the vacuum level during aspiration. The microprocessor integrates the vacuum readings over time during the aspiration cycle to provide a pressure integral for each test sample aspiration. A pressure integral is determined for an unclotted aspiration and is used as a reference for comparison with the pressure integrals of each test sample aspiration to determine whether a blood clot has interfered with the test sample aspiration. Acceptability of the test sample for analysis is based upon a predetermined difference between the reference pressure integral and each test sample pressure integral.

U.S. Pat. Nos. 5,814,275, 5,622,869 and 5,451,373 relate to an apparatus for detecting obstructions of a flow line. A pressure detector detects changes in pressure within a flow cavity, indicating the presence of an obstruction. A barrier is disposed near the pressure detector so that when said flow line and pressure detector expand, the rigid barrier does not expand and the pressure detector is compressed.

U.S. Pat. No. 5,540,081 relates to a pipetting apparatus provided with clot detection comprising a nozzle for aspirating a sample. A pressure sensor and a plurality of pressure difference calculating circuits obtain a pressure difference at a different pressure calculation period. A plurality of discriminating circuits each having a different discrimination threshold value determined according to each of the pressure calculation. An alarm circuit is included for outputting a clot detection alarm signal when at least one of said discriminating circuits discriminates that the obtained pressure difference exceeds the discrimination threshold value.

U.S. Pat. No. 5,503,036 relates to an obstruction detection circuit for detecting an obstruction of a sample probe of an automated fluid sample aspiration/dispensation device and a method for detecting such an obstruction. In one embodiment, the obstruction detection circuit includes a pressure sensor measuring the pressure in a fluid conduit connecting a pump and to a sample probe orifice. The pressure within the connecting fluid conduit is measured shortly after the start of the aspiration or dispensation of a sample volume by the automated fluid sample aspiration-dispensation device. The pressure within the connecting fluid conduit is again measured after the completion of the aspiration or the dispensation by the pump, and if the pressure has not returned to a predetermined range within a predetermined amount of time, an error condition is reported.

U.S. Pat. No. 5,463,895 discloses provides an apparatus and method of detecting non-homogeneity in a fluid sample, such as the presence of foam or bubbles on the surface of the sample, and/or the presence of clots on the surface or in the bulk of the sample. This method involves determining the ambient air pressure within a pipettor, aspirating air into the pipettor as the pipettor moves towards a sample in container and monitoring for a pressure change in the pipettor to indicate the surface level of the fluid in said container. The pipettor is immersed in the fluid and a volume of fluid is withdrawn from the container; pressure changes are monitored after aspiration and compared to predetermined normal aspiration pressure windows.

Liquid aspiration quality determining processes like described are not satisfactory in all instances. For example, many systems for determining the quality or integrity of an aspiration process depend on measuring differences in vacuum pressure at different pre-determined intervals during the aspiration process and comparing a vacuum pressure values to a range of predetermined satisfactory values. Other systems compare derivatives of a vacuum pressure profile to a range of predetermined satisfactory values. As the state of the art advances, aspirated sample volumes become smaller and smaller, causing pressure differential values for liquids with different viscosities become more erratic or "noisy". In addition, pressure profiles of certain higher viscosity liquids do not reach stable end-point values. Hence, there is a need for an improved method for determining the quality of a liquid aspiration process that is effective for small aspiration volumes that may contain an unwanted clot or be insufficient, in the instance of a "short sample".

SUMMARY OF THE INVENTION

It is therefore an object of this invention to provide a liquid aspiration method which is capable of ascertaining the overall quality and integrity of the amount of liquid which has been aspirated into a pipette tip. This is accomplished by determining the quality of the aspirated sample through analysis of the pressure profile generated during a steady state of the aspiration process. Sensed aspiration pressure data used for verification of the overall quality of the aspiration process are recorded for each sample aspiration and analyzed immediately following the aspiration event. Pumping resource motion is started a specified number of reads after data collection has started. The present aspiration method checks the aspiration for undesirable events such as partial or complete clogs, or aspiration of air by calculating the standard deviation of the residuals from a linear regression analysis of the aspiration pressure profile, optionally including a pressure difference test to verify liquid was aspirated. It has been discovered that if the standard deviation of the residuals is less than a predetermined value, then the aspiration process is free of undesirable events.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
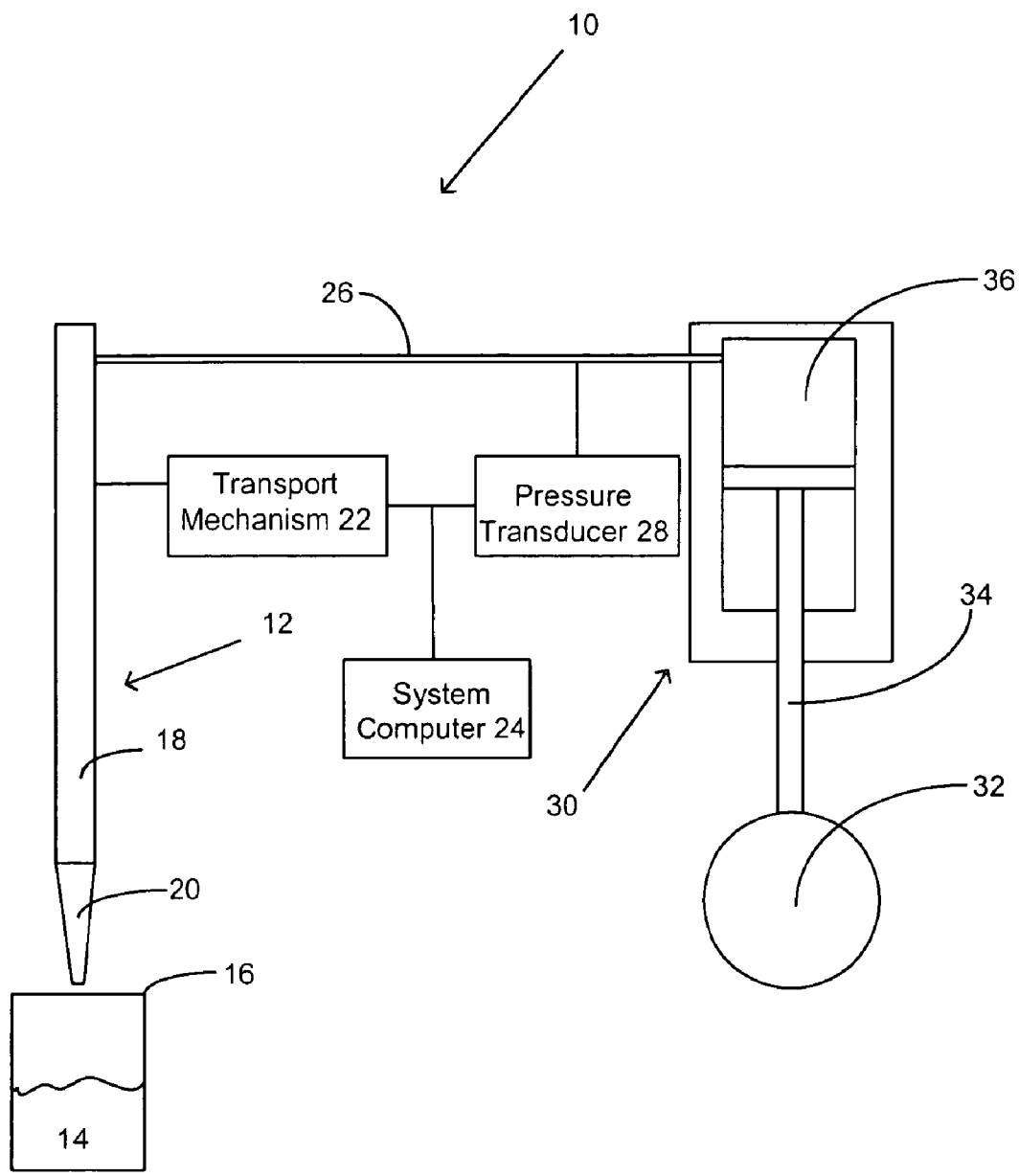
FIG. 1 is a schematic representation of an aspiration system in which the present invention may be practiced.

FIG. 1 illustrates a conventional liquid aspiration system 10 useful in practicing the present invention which includes a pipette 12 for aspirating and dispensing liquid such as a sample liquid 14 stored in a reservoir 16. Although one such sample liquid 14 is shown for the purpose of describing the liquid dispensing system 10, it will be apparent to those skilled in the art that any number of sample liquid reservoirs can be present in an automated clinical analyzer. In an exemplary embodiment, the liquid aspiration system 10 may be used in an automated clinical analyzer (not shown). Such automated clinical analyzers are well known in the art and those skilled in the art will know with certainty the functions of the elements of the analyzers to which reference is made.

Pipette 12 generally includes a central cavity 18 which may be adapted to carry a replaceable pipette tip 20 which may have a conically narrowing nose shape terminating in a distal orifice 40 through which liquid is aspirated into cavity 18, and through which liquid is dispensed therefrom. Central cavity 18 opens into the tip cavity upon engagement of the holder with the tip. Alternately, pipette tip 20 may be integral with central cavity 18. Aspiration system 10 further comprises an aspiration/dispensing pressure control 30 adapted to produce a vacuum pressure within cavity 18 during aspiration and a positive pressure during dispensing. Pressure source 30 is connected to pipette by tubing 26 and the pressure therein is monitored with a conventional pressure transducer 28 interfaced to a system computer 24 programmed to practice the present invention. Typical of pressure source 30 is a piston assembly 34 connected with tubing 26 and the pipette 12 on a top side thereof, opposite pipette tip 20. Aspiration systems 10 like seen in FIG. 1 are well known to those skilled in the art and may be concocted with a variety of components and designs. Practicing the present invention requires only that pressure be used to cause liquid aspiration and dispensing from pipette 12 and that the aspiration pressure be monitored.

Liquid aspiration system 10 typically includes a transport device 22, indicated diagrammatically, which may be of any suitable type. The transport device 22 is capable of moving the pipette 12 laterally (the X-direction), vertically (the Z-direction) and from front to back (the Y-direction) in an analyzer to enable the pipette 12 to pick up a pipette tip 20 (when disposable tips are used), aspirate liquid 14 into the pipette tip 20 from a sample liquid reservoir 16 or tube 16 and to dispense a desired amount of sample liquid into a test assay element or other container (not shown). Generally, stepper-motors, electronic drivers, interface circuits and limit-switches are used within transport device 22 to control transporting the pipette 12 and these are interfaced to system computer 24. Alternately, pipette 12 may be translated along the vertical z-axis by a rack-and-pinion drive. Conventional electronics are used to interface the transport device to the computer 24.

As shown, pipette 12 has a cavity 18 for holding liquid 14 and a tube 26 connected therefrom to a vacuum pressure measurement device or transducer 28 and to pressure control 30 for producing a variable vacuum pressure throughout the pipette 12 responsive to commands from computer 24. Such devices and sources are well known in the art. Commercially available pipettes 12 made from metals like stainless steel or plastics like polypropylene and similar materials, and tubing 26 made from vinyl, polypropylene, polyethylene, metal, etc, may used in the present invention. Pressure measurement device 28 measures air pressure within the pipette 12 both continuously and periodically during the aspiration method of the present invention. An exemplary pressure measurement device 28 is a pressure transducer (Model SCXL004DN from SenSym, Miltipas, Calif.) and it is interfaced to the computer 24 to provide a measured air pressure within tubing 26 to computer 24.

An exemplary aspiration pressure control 30 is a piston-syringe device, mechanically connected to a stepper motor 32 and encoders or home limit-switches (not shown) capable of controlling the movement of the syringe piston and causing pressure control 30 to aspirate and dispense air through tubing 26. Aspiration pressure control 30 and pressure sense device 28 are electronically interfaced to computer 24 which is used to control the operation of the liquid aspiration system 10. The computer 24 also provides signals to control the movement of the pipette 12 via transport device 22 as well as the aspiration into, and dispensing of liquid from, the pipette tip 24.

In such an instance, as illustrated in FIG. 1, pressure control 30 comprises a piston 34 attached to motor 32 for advancing and retracting the piston 34 within a closed chamber 36. A downward movement of piston 34 tends to increase the volume of the chamber 36, thereby to create vacuum or negative air pressure within the chamber 36 which draws air from the interconnected tubing 26, cavity 18, and pipette tip 20 into cavity 18 for aspirating liquid 14 into pipette tip 20. Advancing piston 34 into chamber 36 decreases the volume of chamber 36, thereby to provide a positive air pressure which pushes air out of chamber 36 into the interconnected tubing 26, cavity 18, and pipette tip 20 for expelling and dispensing liquid from the pipette tip 20 via the tip orifice. Thus, the piston 34 provides for aspiration of liquid into, and dispensing of liquid from, the pipette tip 20.

Tubing lengths and diameters of tubing 26 are selected to provide appropriate dynamic response of the pressure system to allow for proper level sensing and aspiration checking. The length of tubing 26 between the aspiration pressure control means 30 and the pipette 12 provides the majority of the pressure head loss in the system 10. The length of tubing between the aspiration pressure control means 30 and the pump provides sufficient pressure damping to reduce the pressure noise generating by the individual pump steps during operation of the pipette 12.

In accordance with the present invention, aspiration pressure control 30 and pressure sense device 28 are controlled and analyzed by computer 24 so as to determine the quality of the aspirated sample liquid 14 through analysis of a pressure profile generated during the aspiration process. The aspiration quality verification method has the ability to detect adverse events such as insufficient sample liquid 14, a clogged pipette tip 20, aspiration of air or air bubbles, aspiration of a clot or other obstruction along with the sample, and aspiration of a gel or cell layer in a centrifuged sample container, among other conditions. Herein, the term "proper aspiration" describes an aspiration free of such adverse events having a "proper profile" and the term "improper aspiration" describes an aspiration experiencing any of such adverse events and having an "improper profile". By providing the ability to detect other aspiration errors between the extremes of a fully clogged or fully open pipette tip 20, the present invention provides additional protection against supplying an analyzer with a low quality aspirated liquid sample.

A key feature of the present invention is analyzing pressure measurements from pressure transducer 28 only during the initial portion of an aspiration process without requiring pressure measurement after the aspiration process is completed. Aspiration pressure transducer 28 is activated only for a specified number pressure measurement reads from pressure transducer 28. Pressure data, for instance using an A/D (analog signals converted to digital data) converter, are collected for a period long enough to capture only an initial portion the entire aspiration process. The pressure data are collected in real time during the aspiration cycle. In a typical embodiment, an analog input subsystem reads the pressure sense device at a constant rate (for example, 500 Hz) time stamping each reading and buffering the reading(s) for eventual inclusion into the aspiration data set. In parallel to the aspiration process, the pressure data are periodically transferred from the analog sub-system buffer into the aspiration data set. The aspiration data set consists of a series of time stamped pressure readings that occur before and during the initial portion of pump operation. Each process event (start of aspiration cycle, start of pump cycle, end of aspiration pressure readings) is marked in the data set. To achieve close coupling with process event, the data are also read from the analog sub-system coincident with these events. The resultant aspiration data set then contains a multiple of time stamped pressure and event markers that allow analysis of the overall quality of the aspiration process.

Sensing of the upper surface portion of the sample liquid 14 may be performed via system 10 using capacitive level sensing techniques known in the art and like that described in U.S. patent application Ser. No. 11/085,660, now U.S. Pat. No. 7,150,190. The technique disclosed therein confirms that a change in capacitance within a liquid level sensor is caused only by true physical contact between a probe and a liquid by verifying that any change in capacitance of the liquid level sensor is repeatable and constant over a given time period and thereby is caused by actual contact the probe and liquid and is not caused by spurious electrical disturbances or other measuring irregularities.

Once liquid level in the reservoir 16 has been determined, sample aspiration commences. A vacuum generated by the aspiration pressure control 30 draws sample liquid 14 up into the pipette tip 20. At the sample time, pipette 12 descends to follow the level of the sample down in reservoir 16, keeping the tip 20 immersed in liquid 14. Different descent rates are used, depending on the diameter of the reservoir 16. After aspiration is completed, the pressure profile recorded during an initial portion of the event is examined as described hereinafter and pipette tip 20 is retracted from liquid sample 14. Finally, a quantity of air may be aspirated into tip 20 to move aspirated sample liquid 14 away from the bottom of tip 20 to prevent potential drips.

The rate of aspiration is chosen to provide a pressure profile with the features necessary for aspiration success analysis described below while minimizing cycle time and keeping the magnitude of the pressure signal within the limits of the pressure transducer 28.

Figure 2:
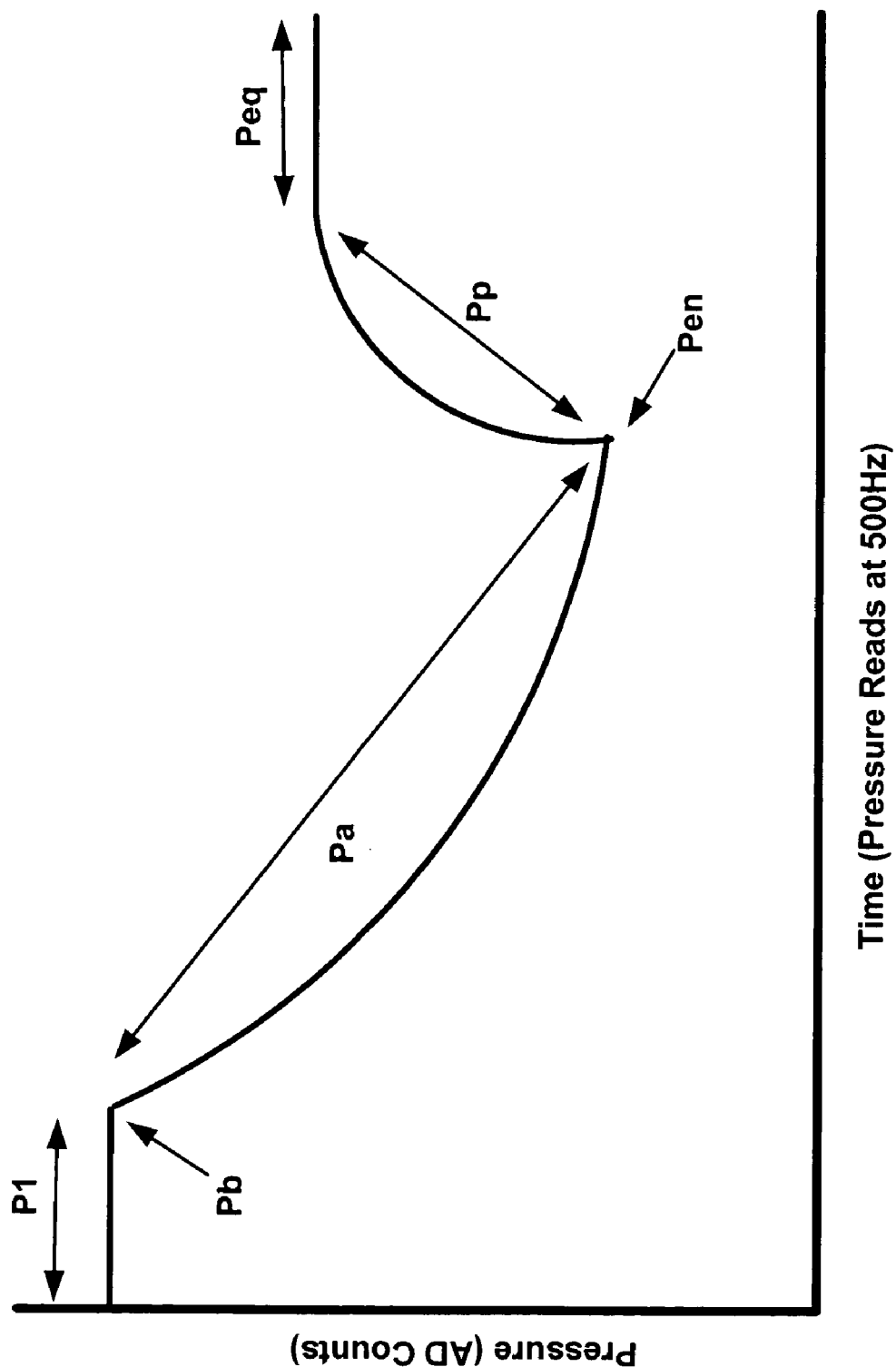
FIG. 2 is a graphical representation of a typical aspiration pressure profile obtainable with the aspiration system of FIG. 1.
Figure 3:
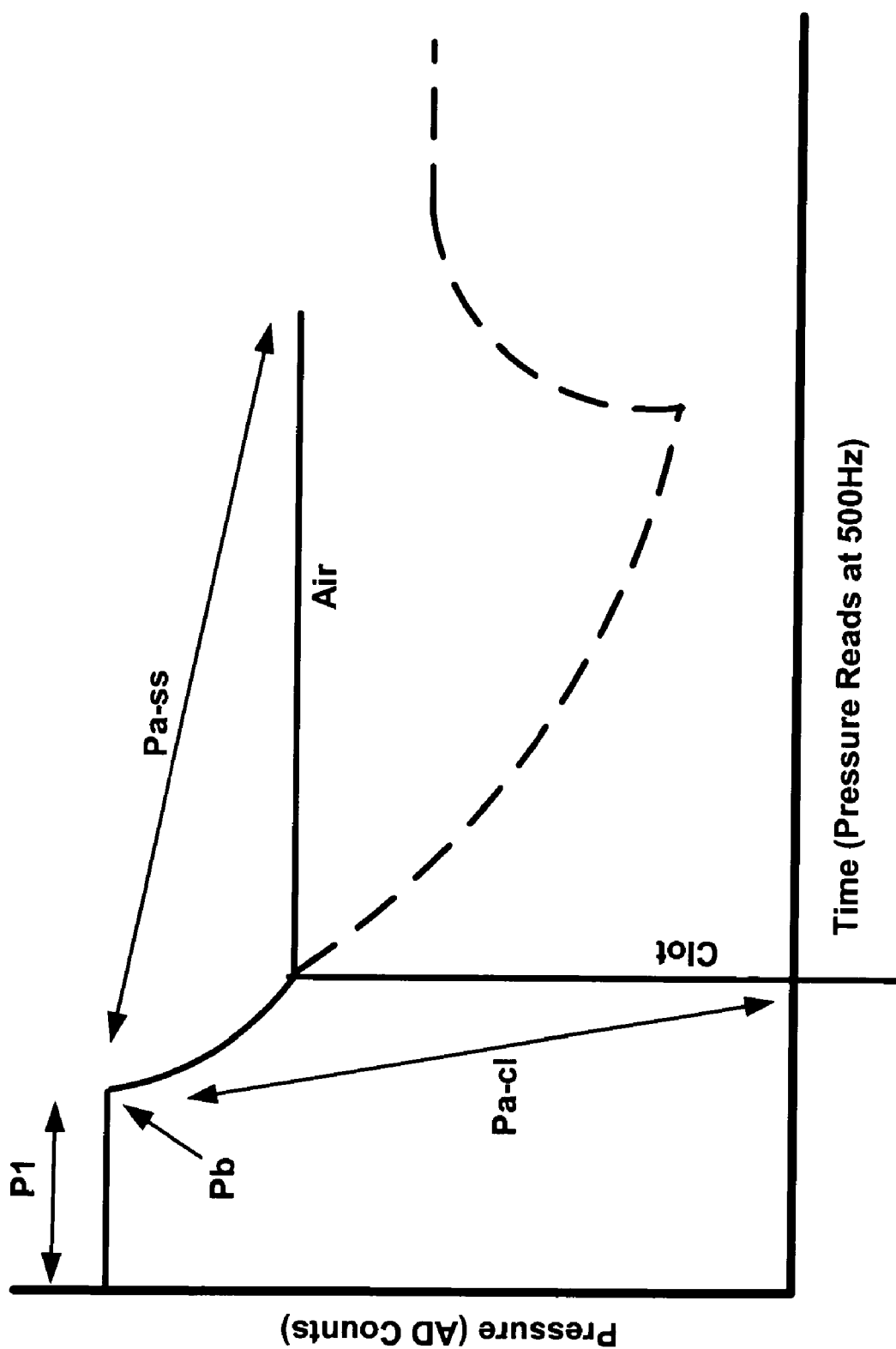
FIG. 3 is a graphical representation of an aspiration pressure profile obtainable with the aspiration system of FIG. 1 illustrating the presence of clots or a short sample.

FIG. 2 is illustrative of the well-known aspiration pressure profile that has been used in the prior art to ascertain the quality of the aspiration process utilizing some combination of the following events:

P1=averaged relative pressure prior to actual aspiration of liquid into pipette 20
Pb=relative pressure at beginning of actual aspiration of liquid into pipette 20
Pa=pressure measurement range during actual aspiration
Pen=relative pressure at end of actual aspiration of liquid into pipette 20
Pp=pressure prior to equilibrium
Peq=relative pressure at equilibrium The present invention checks the aspiration process for adverse events such as clots in the sample sufficiently large to block the distal orifice 40 or the aspiration of air due to a sample being short. The invention is based on the fact that, during the Pa range described above in conjunction with FIG. 2, if a clot is encountered, the pressure measured by pressure transducer 28 will increase sharply as indicated by downwardly pointed arrow identified as "Clot" in FIG. 3. (The value actually rises too far to be illustrated on FIG. 3) The solid line marked Pa-cl thus indicates the aspiration pressure profile of an improper aspiration due to the presence of a clot blocking the distal orifice 40 after the beginning of aspirate. In the alternative, if a short sample is encountered, the pressure measured by pressure transducer 28 will level off as indicated by the horizontal line identified as "Air" in FIG. 3. during the period of time indicated by the solid line marked Pa-ss identifying the aspiration pressure profile of an improper aspiration due to a short sample The dashed line in FIG. 3 is indicative of a proper aspiration process and is included to contrast the overall shape of proper and improper aspiration processes. As is well known, one of the parameters affecting an aspiration process is the desired volume of aspirated liquid 14. Computer 24 is programmed, among other operations, to control the operation of the liquid aspiration system 10 to deliver such a desired volume, in particular by operating aspiration pressure control 30 for a predetermined length of time after Pb is established. This is the period of time, the "aspiration cycle time" during which pressure measurements are made during aspiration, ending at a point in time at which Pen, pressure at end of aspiration, is achieved.

An aspiration is unsuccessful when the pressure-time profile during aspiration does not match that the desired pressure profile obtained for a liquid in the absence of abnormalities or non-uniformities. The degree of match may be obtained using any of a number of well-known numerical analysis techniques which approximate actual computations of an integral representing the difference between the measured pressure profile and the pressure profile in the absence of abnormalities or non-uniformities. As is known, every definition of an integral is based on a particular measure: the Lebesgue integral is based on Lebesgue measure and the Riemann integral is based on Jordan measure. The study of measures and their application to integration is known as measure theory. In general, these techniques are some form or another of a Lebesgue integral which is defined in terms of upper and lower bounds of the functions to be compared using the Lebesgue measure of a set. It uses a Lebesgue sum of the Lebesgue measures of the set of points for which values are approximated. This type of integral covers a wider class of functions than does the Riemann integral, the integral popularly encountered in calculus texts and used by physicists and engineers. Newton-Cotes formulas are another straightforward family of numerical integration techniques. To integrate a function over some interval, it is divided into equal parts and polynomials which approximate the tabulated function are determined and integrated to approximate the area under the curve. Lagrange interpolating polynomials are used to find the fitting polynomials. The resulting formulas are called Newton-Cotes formulas, or quadrature formulas. If the function is given explicitly instead of simply being tabulated at the values, the best numerical method of integration is called Gaussian quadrature. By picking the intervals at which to sample the aspiration pressure, this procedure produces more accurate approximations of the variance between actual and desired pressure profiles (but is more complicated to implement).

Alternately, Simpson's rule, a Newton-Cotes formula, can be used to approximate the integral of variance between actual and desired pressure profile by using quadratic polynomials (i.e., parabolic arcs instead of the straight line segments used in the trapezoidal rule). Simpson's rule can be derived by integrating a third-order Lagrange interpolating polynomial fit to the function at three equally spaced points. Since it uses quadratic polynomials to approximate functions, Simpson's rule actually gives exact results when approximating integrals of polynomials up to cubic degree.

A Gaussian quadrature can be alternately employed to obtain the best numerical estimate of the pressure variance by picking optimal abscissas at which to evaluate the function. The fundamental theorem of Gaussian quadrature states that the optimal abscissas of the m-point Gaussian quadrature formulas are precisely the roots of the orthogonal polynomial for the same interval and weighting function. Slightly less optimal fits may be obtained from Radau quadrature or Laguerre quadratures. Techniques such as these may be employed to advantage in performing the present invention, however, because the degree of accuracy in determining the extent to which the measured pressure-time profile during aspiration does not match the pressure-time profile known to be achieved for a liquid in the absence of abnormalities or non-uniformities is but a relative measure, a less sophisticated numerical analytical technique, known as standard deviation of the residuals may be employed.

The difference between the measured profile and the expected profile is at a particular time the residual at that time. The standard deviation of the residuals over the time of a profile measures the fit or lack of fit between a profile in the absence of abnormalities or non-uniformities and the measured profile. However, low standard deviation of the residuals is not by itself an indicator of a successful aspirate.

The residuals can consist of both random error and systematic error parts referred to as the variance error and the bias error. (N. R. Draper and H. Smith, "Applied Regression Analysis," John Wiley & Sons, 1966, pp. 36 . . . ) For the present invention either error indicates an abnormality or non-uniformity of the aspirated liquid. A high standard deviation of the residuals would suggest that the sample was abnormal or had non-uniformities. There are a number of other well-known mathematical procedures for testing that the standard deviation of the residuals does or does not exceed a given value. (Abraham Wald, "Sequential Analysis," Dover Publications, 1947, pp. 125 . . . )

Figure 4:
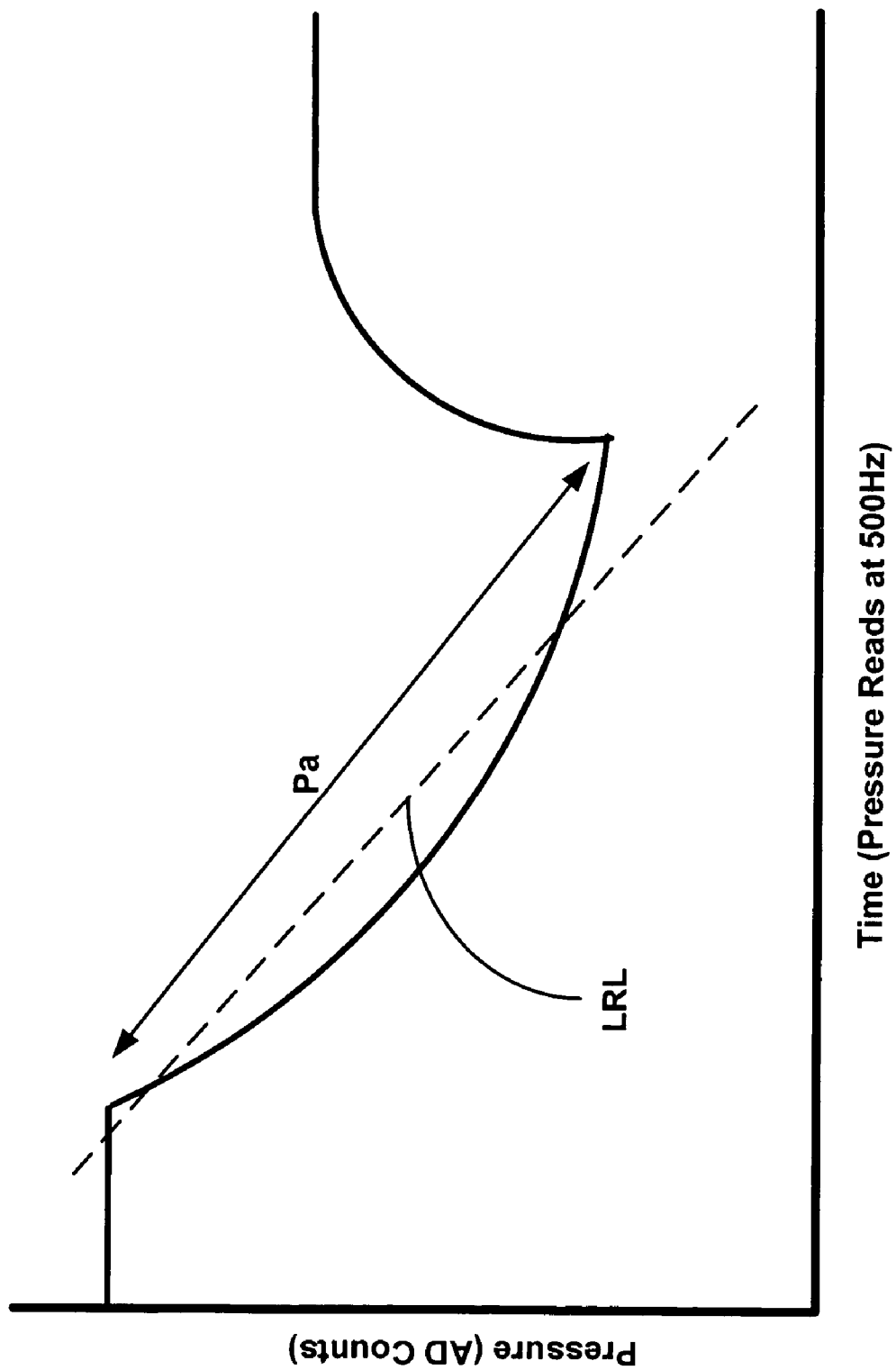
FIG. 4 is a graphical representation of an aspiration pressure profile obtainable with the aspiration system of FIG. 1 illustrating a linear regression analysis of a proper aspiration pressure profile, in accord with the present invention.

To ascertain the presence of a clot during aspiration, in accordance with the present invention, pressure data are obtained by pressure transducer 28 during the relatively "straight line" or "steady state" portion Pa of a "normal" aspiration pressure profile obtained from a sufficiently large sample without clots like shown in FIG. 4. Using these pressure data, a linear regression analysis is conducted in order to determine the slope b and intercept a of the general regression equation when written as Y=a+b X, in this case, Y=pressure and x=time of aspiration. The results of such a calculation is seen in FIG. 4 as dashed line LRL. Next, the variation between the actual and theoretical pressure data is mathematically determined using any of a number of numerical techniques like discussed above.

In an exemplary embodiment, the residual variance is calculated as a measure of the variation of the actual pressure values about the linear regression line LRL. Residual Variance RV is given by the following equation where y is the actual measured pressure value, y' is the pressure calculated by the SLR formula, y-y' is the residual, and n is the number of data points.

$$(RV)^2 = \frac{\sum (y-y')^2}{n-2}$$

The square root of the Residual Variation is the standard deviation of the estimated residuals. It has been discovered that if the standard deviation of the residuals (y-y') is greater than a predetermined value, then either a clot within the liquid sample 14 blocked the distal orifice 40 after the start of aspirate into pipette 12 or there was insufficient sample to aspirate the desired volume. This predetermined value may be experimentally determined by aspirating a liquid sample having a gelatinous material mixed into an aqueous sample and calculating the standard deviation of the residuals for such an improper aspiration.

Figure 5:
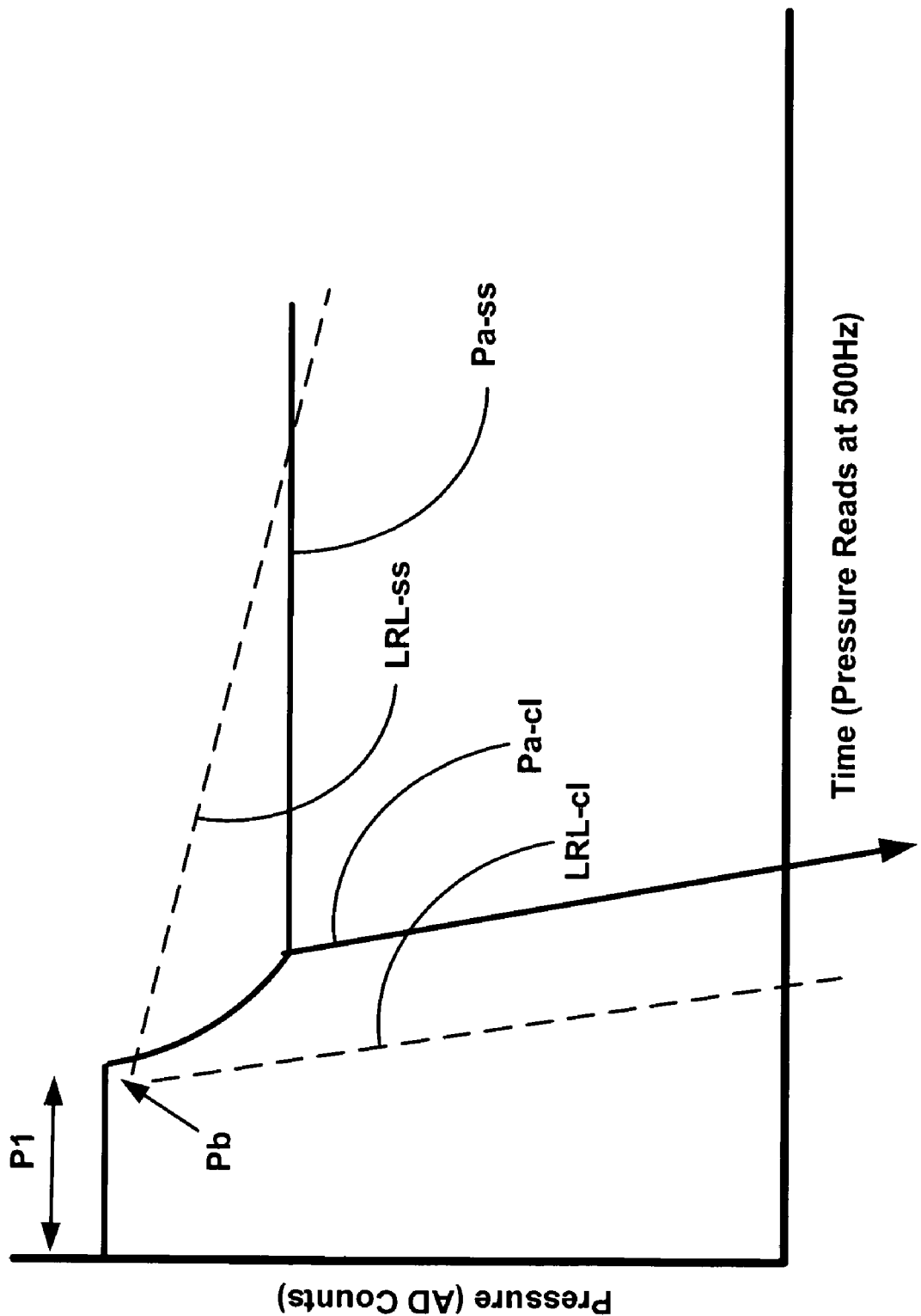
FIG. 5 is a graphical representation of an aspiration pressure profile obtainable with the aspiration system of FIG. 1 illustrating a linear regression analysis of two improper aspiration pressure profiles, in accord with the present invention.

FIG. 5 is a graphical representation of an aspiration pressure profile obtainable with the aspiration system of FIG. 1 illustrating a linear regression analysis of two improper aspiration pressure profiles obtained in accord with the present invention. The solid line marked Pa-cl indicates the aspiration pressure profile of an improper aspiration due to the presence of a clot blocking the distal orifice 40 after the beginning of aspirate and the dashed line marked LRL-cl is indicative of a simple linear regression analysis of data points along aspiration pressure profile of Pa-cl. Similarly, the solid line marked Pa-ss indicates the aspiration pressure profile of an improper aspiration due to a short sample (aspiration of air or bubbles) and the dashed line marked LRL-ss is indicative of a simple linear regression analysis of data points along aspiration pressure profile of Pa-ss. A calculation of the standard deviation of the residuals for the LRL of the proper aspiration profile of FIG. 4 and of the standard deviation of the residuals for LRL-cl and LRL-ss for the two improper aspiration profiles of FIG. 5 is basically an indication of the total gap between SLR, SLR-cl and SLR-ss and their respective pressure profiles Pa-pa, Pa-cl and Pa-ss. What is clear from an examination of these residuals analyses is that the residuals of the LRL of a proper pressure profile will be smaller than the residuals of the LRL of an improper pressure profile.

The present invention thus provides a method for ascertaining or confirming that an aspiration process has been conducted for a sample that is free of adverse effects due to an insufficient sample 14, a clot at the distal orifice 40 of the clogged pipette tip 20, or aspiration of air or air bubbles without requiring that pressure values be evaluated for the entire aspiration process as is routine in the prior art. This improvement thus provides a simplified method for verifying the integrity of a fluid transfer and can be further characterized by measuring the aspiration pressure profiles of a number of liquid sample containing known amounts of a gelatinous material and calculating the standard deviation of the residuals for a series of such improper aspirations. Due to multiple variations in aspiration system designs, (for example, variations in central cavity 18, pipette tip 20, pressure source 30, tubing 26, pressure transducer 28 and the like), it is not possible to determine a universally applicable "break point" of residual values. A calibration process to determine the range of residual standard deviations associated with "proper aspiration profiles" is well within the ability of those skilled in the art.

Figure 6:
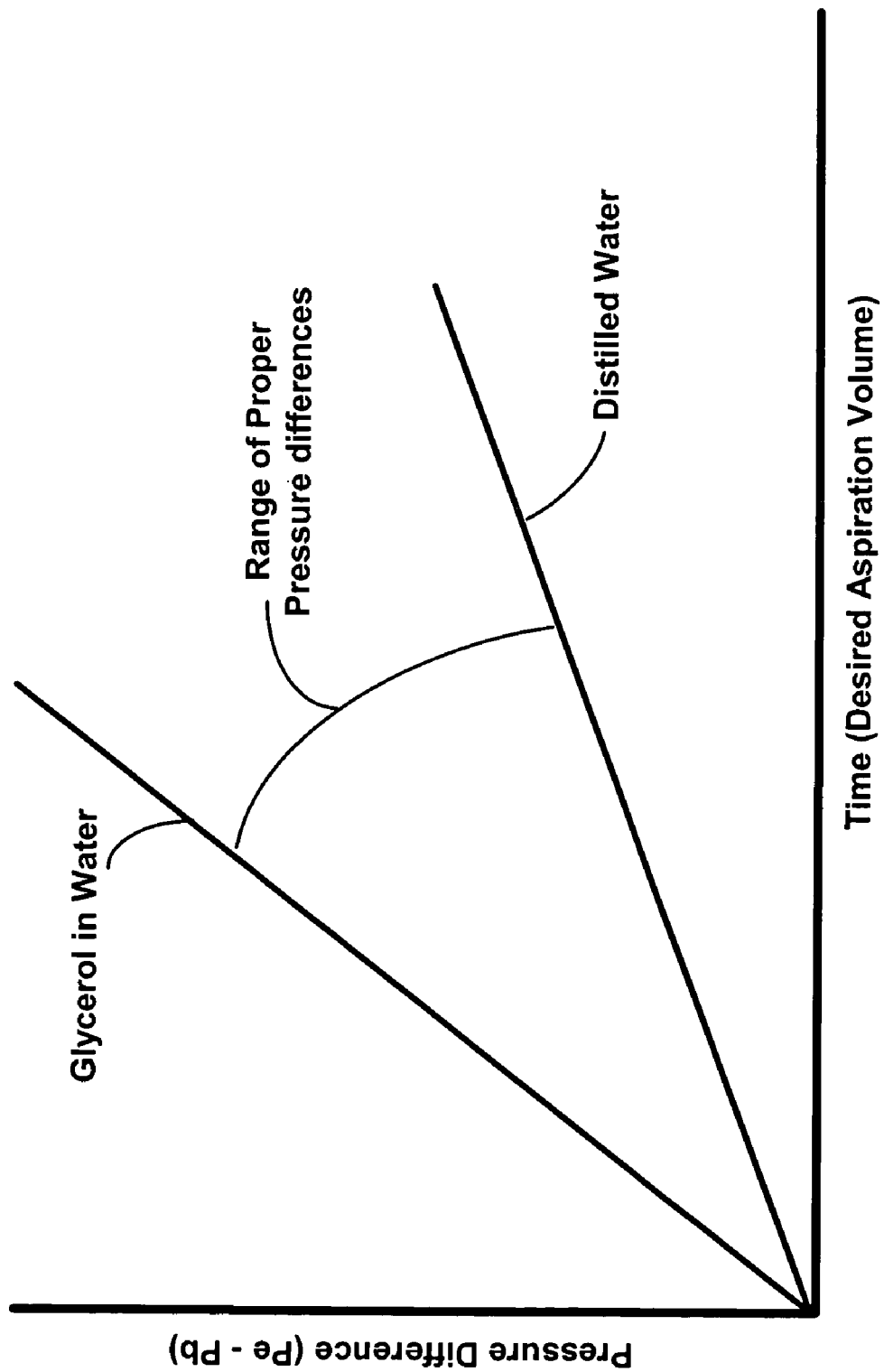
FIG. 6 is a calibration pressure difference range measured as a function of aspiration volume for the aspiration system of FIG. 1.

An initial evaluation of the aspiration profile may be accomplished by simply comparing the aspiration pressure values before and after the "aspiration cycle time". As described earlier, the "aspiration cycle time" is that period of time between the onset of aspiration Pb and that point in time at which Pen, pressure at end of aspiration, is achieved. Because a specified amount of liquid 14 is desired to be aspirated, pressure source 30 will be operated for a predetermined amount of time after Pb is established. Thus a comparison of the relative pressure values Pb and Pen (essentially the actual aspiration beginning and ending pressure values) can be used to ascertain if there is sufficient sample liquid 14 to meet the desired aspiration volume or if there was a definite clot in the aspirated liquid. As seen in FIG. 6, for any given aspiration system 10, a tube of distilled aqueous liquid 14 can be aspirated and the a calibration pressure difference (Pen-Pb)$_{cal}$ can measured as a function of desired aspiration volume. If actual pressure difference (Pen-Pb)$_{act}$ is less than calibration pressure difference (Pen-Pb)$_{cal}$, it can be assumed that air was aspirated due to a short sample. Similarly, since no human fluid sample are more viscous than a 68% solution of glycerol in distilled water, for example, if actual pressure difference (Pen-Pb)$_{act}$ is greater than calibration pressure difference (Pen-Pb)$_{cal}$, it can be assumed that a clot has blocked the distal orifice 40 of the pipette tip 20 from almost the beginning of the aspirate.

Those skilled in the art will appreciate that the embodiments of the invention disclosed herein are illustrative of the principles of the invention and that other modifications may be employed which are still within the scope of the invention. For example, the variance of the measured pressure-time profile during aspiration from that of a profile in the absence of abnormalities or non-uniformities may be obtained to a higher degree of accuracy using more sophisticated numerical integration techniques, like Newton-Cotes formulas, Simpson's rule or Gaussian quadrature. Obvious variants of the invention should also be applicable to a fluid-coupled system with a few adjustments to the parameters. The method also could be applied to the fluid dispensing process to determine success of the dispense operation. The method could also be adjusted to distinguish between fluid types; for example, normal serum from whole blood. Given the known relationship between sample volume and pump displacement, the method could also be used to aspirate a variable volume. Accordingly, the present invention is not limited to those embodiments precisely shown and described in the specification but only by the following claims.

What is claimed is:

1. A method for verifying that an aspiration process for aspirating a liquid between a pipette and a container is free of the adverse affects of clots in the liquid or of an insufficient liquid volume by:
    (1) determining the actual profile of an aspiration pressure curve for a pipette used in the aspiration process;
    (2) determining a mathematical representation of the determined actual profile of the aspiration pressure curve;
    (3) using numerical analysis to determine whether or not the difference between the actual profile of the aspiration pressure curve and the mathematical representation of the actual profile of an aspiration pressure curve is less than the standard deviation of the residuals of linear regression analysis of an aspiration pressure curve measured for either:
        (a) a sample known to have clots; or
        (b) a sample known to be less than a desired aspiration volume; and,
    (4) using the results of the numerical analysis to confirm that the aspiration process has been performed using a liquid that is free of adverse affects.

2. A method for verifying that an aspiration process for aspirating a liquid between a pipette and a container is free of the adverse affects of clots in the liquid or of an insufficient liquid volume by:
    (1) determining the actual profile of an aspiration pressure curve for a pipette used in the aspiration process between the onset of actual aspiration and the end of actual aspiration;
    (2) confirming that the difference in aspiration pressure between the onset of actual aspiration and the end of actual aspiration falls either within or outside of a specific range of aspiration pressures;

(3) determining a mathematical representation of the actual profile of an aspiration pressure curve by performing a liner regression analysis on the actual profile of the aspiration pressure curve when the difference in aspiration pressure between the onset of actual aspiration and the end of actual aspiration falls within the specific range of aspiration pressures;

(4) using numerical analysis to determine whether or not the difference between the actual profile of the aspiration pressure curve and the mathematical representation of the actual profile of the aspiration pressure curve is less than the standard deviation of the residuals of linear regression analysis of an aspiration pressure curve measured for either a sample known to have clots or a sample known to be less than a desired aspiration volume; and (5) using the results of the numerical analysis to confirm that the aspiration process has been performed using a liquid that is free of adverse affects.

3. A method for verifying that an aspiration process for aspirating a liquid between a pipette and a container is free of the adverse affects of clots in the liquid or of an insufficient liquid volume by:

(1) determining the actual profile of an aspiration pressure curve for a pipette used in the aspiration process between the onset of actual aspiration and the end of actual aspiration;

(2) determining that the difference in aspiration pressure between the onset of actual aspiration and the end of actual aspiration falls either within or outside of a specific range of aspiration pressures;

(3) determining a mathematical representation of the actual profile of the aspiration pressure curve by performing a liner regression analysis on the actual profile of the aspiration pressure curve when the difference in aspiration pressure between the onset of actual aspiration and the end of actual aspiration falls with in the specific range of aspiration pressures;

(4) confirming that the difference in aspiration pressure between the onset of actual aspiration and the end of actual aspiration falls within the range of aspiration pressures defined by:
  (a) the aspiration pressure for the onset of actual aspiration for a sample of liquid distilled water and a sample of a liquid mixture of water and glycerol; and,
  (b) the aspiration pressure for the end of actual aspiration for a sample of liquid distilled water and a sample of a liquid mixture of water and glycerol; and, (5) using the results of whether the difference in aspiration pressures falls within the defined range of aspiration pressures in order to confirm that the aspiration process has been performed using a liquid that is free of adverse affects.

* * * * *